United States Patent [19]
Lapointe et al.

[11] Patent Number: 5,639,235
[45] Date of Patent: Jun. 17, 1997

[54] METHOD FOR SELECTING TEETH FOR THE PRODUCTION OF DENTURES OR THE LIKE

[76] Inventors: Yves Lapointe, 2281 Bédard, Longueuil, Québec, Canada, J4N 1B4; Ghislain Lapointe, 603 Des Récollets, Longueuil, Québec, Canada, J4L 3E1

[21] Appl. No.: 227,622

[22] Filed: Apr. 14, 1994

[30] Foreign Application Priority Data

Jul. 7, 1993 [CA] Canada .................................. 2100009

[51] Int. Cl.⁶ .................................................. A61C 19/10
[52] U.S. Cl. ............................. 433/26; 433/215; 433/229
[58] Field of Search ................................ 433/26, 202.1, 433/203.1, 213, 215, 229

[56] References Cited

U.S. PATENT DOCUMENTS 4,799,888  1/1989  Golub ........................................ 433/215

*Primary Examiner*—Edgar S. Burr
*Assistant Examiner*—Steven S. Kelley
*Attorney, Agent, or Firm*—Swabey Ogilvy Renault

[57] ABSTRACT

A method for determining the size, shape and position of a pair of upper central incisors for the production of dentures comprises the steps of covering the patient's upper gums with a paste, providing a series of representations of different pairs of upper central incisors and positioning different ones of these representations on the paste until a representation of desired size and shape is selected and secured to the paste by way of an adhesive at a chosen location thereon. The paste carrying the selected representation is then removed from the patient's mouth, whereby dentures can be produced on the basis of the positioning of the upper central incisors on the paste roll and on the selected model of upper central incisors, as the latter determine the models of the remaining teeth of the dentures. The method can also be used for the determination of an artificial tooth used for a dental implant, a bridge or a crown. Also, a method is proposed for determining the vertical dimension of occlusion with a rest position clearance also for the production of dentures, wherein lower central incisors are positioned with respect to the patient's facial characteristics.

23 Claims, 12 Drawing Sheets

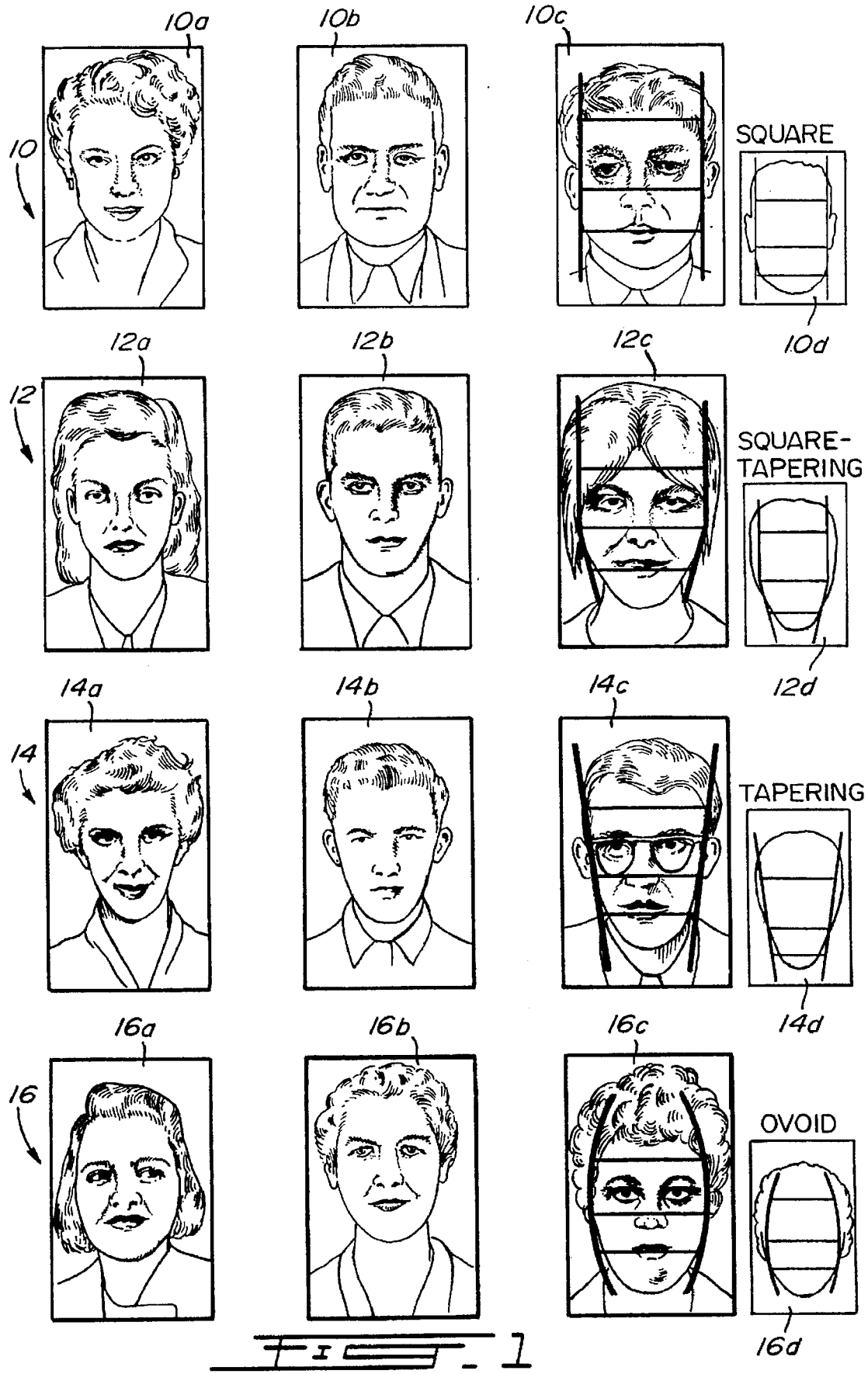

SQUARE

| MODEL IDENTIFICATION NO. | WIDTH OF CENTRALS (mm) | LENGTH OF CENTRALS (mm) | WIDTH OF 6 FRONT CENTRALS (mm) | MOLD |
|---|---|---|---|---|
| 11D | 8,00 | 10,25 | 47,00 | |
| 11G | 8,75 | 11,25 | 52,00 | |
| 11H | 9,25 | 11,50 | 55,00 | |
| 12E | 8,50 | 10,50 | 49,00 | |
| 12F | 8,50 | 10,75 | 50,50 | |
| 12G | 9,25 | 10,75 | 52,50 | |
| 13E | 8,25 | 9,50 | 48,50 | |

11D 11G 11H 12E 12F 12G 13E  SQUARE

SQUARE-TAPERING

| MODEL IDENTIFICATION NO. | WIDTH OF CENTRALS (mm) | LENGTH OF CENTRALS (mm) | WIDTH OF 6 FRONT CENTRALS (mm) | MOLD |
|---|---|---|---|---|
| 21C | 7,75 | 10,25 | 45,00 | |
| 21D | 8,00 | 10,50 | 47,50 | |
| 21E | 9,00 | 12,00 | 51,00 | |
| 21G | 9,75 | 12,00 | 56,00 | |
| 21H | 10,00 | 13,00 | 56,00 | |
| 21J | 10,25 | 12,50 | 58,00 | |
| 21X | 8,75 | 11,00 | 51,00 | |

TAPERING

| MODEL IDENTIFICATION NO. | WIDTH OF CENTRALS (mm) | LENGTH OF CENTRALS (mm) | WIDTH OF 6 FRONT CENTRALS (mm) | MOLD |
|---|---|---|---|---|
| 42D | 8,00 | 10,25 | 46,50 | |
| 42G | 8,75 | 10,50 | 52,00 | |
| 42H | 9,00 | 11,25 | 55,00 | |
| 43D | 7,75 | 8,75 | 46,00 | |
| 43F | 8,75 | 9,50 | 50,00 | |
| 45H | 8,75 | 11,25 | 54,00 | |

42D
42G
42H
43D
43F
45H

TAPERING

—20c

FIG_2C

OVOID
| MODEL IDENTIFICATION NO. | WIDTH OF CENTRALS (mm) | LENGTH OF CENTRALS (mm) | WIDTH OF 6 FRONT CENTRALS (mm) | MOLD |
|---|---|---|---|---|
| 62G | 9,25 | 11,75 | 53,00 | 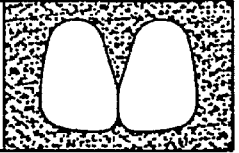 62G OVOID |
20d

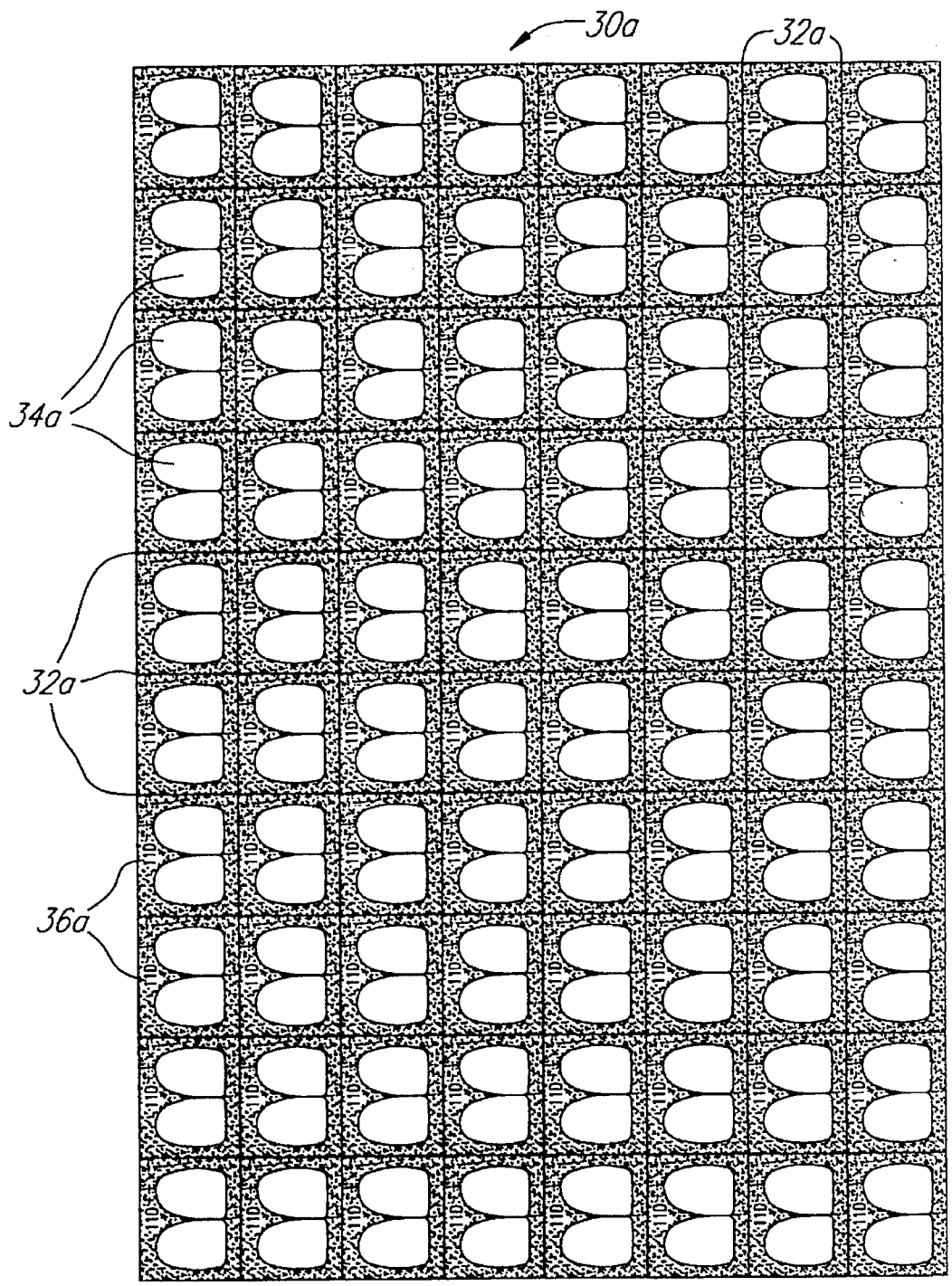
| | WIDTH OF CENTRALS (mm) | LENGTH OF CENTRALS (mm) | WIDTH OF 6 FRONT CENTRALS (mm) |
|---|---|---|---|
| | 8,00 | 10,25 | 47,00 |
SQUARE
11D
FIG_3A

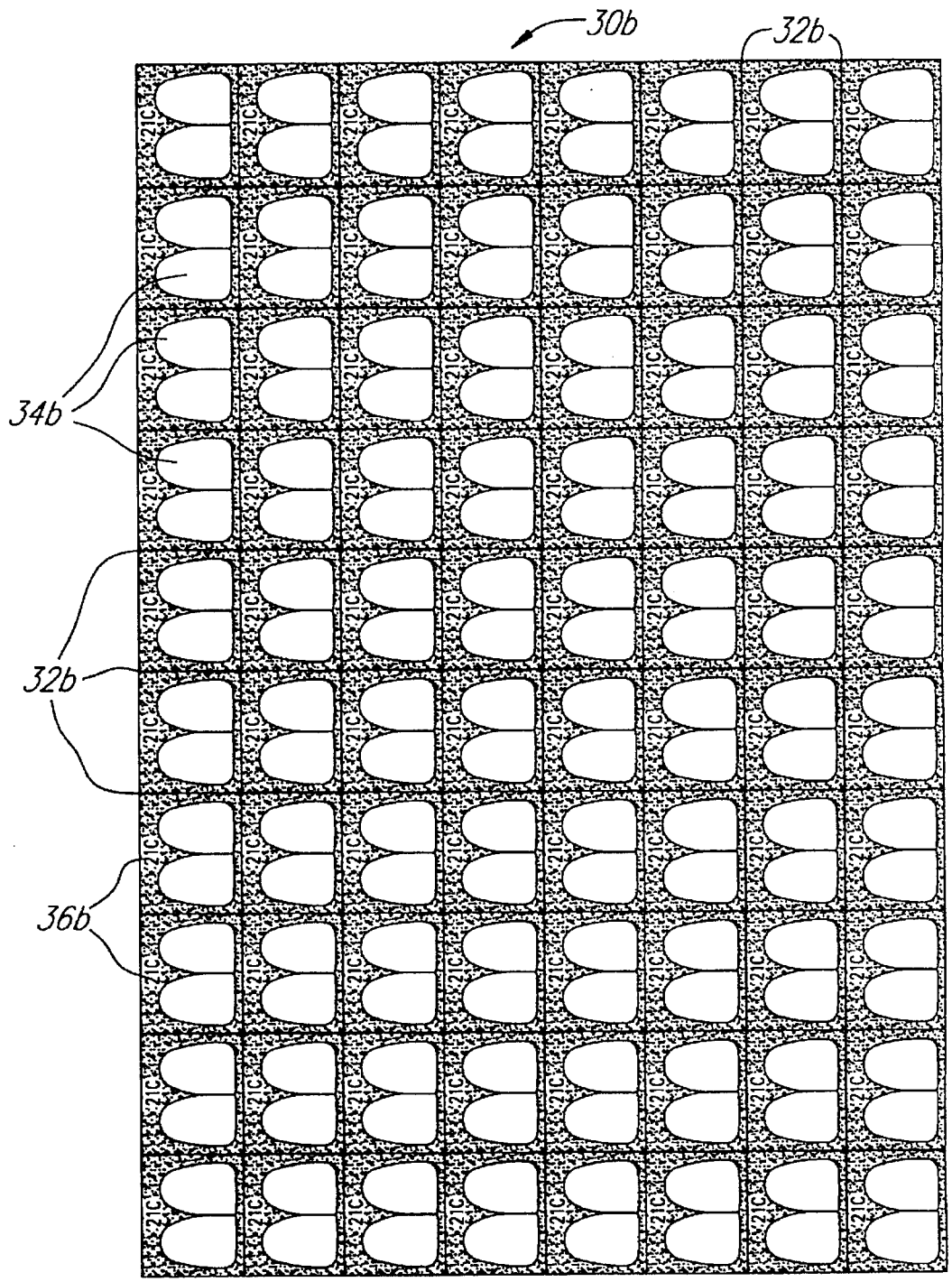
| 38b | WIDTH OF CENTRALS (mm) | LENGTH OF CENTRALS (mm) | WIDTH OF 6 FRONT CENTRALS (mm) |
|---|---|---|---|
| | 7,75 | 10,25 | 45,00 |
SQUARE–TAPERING
21C

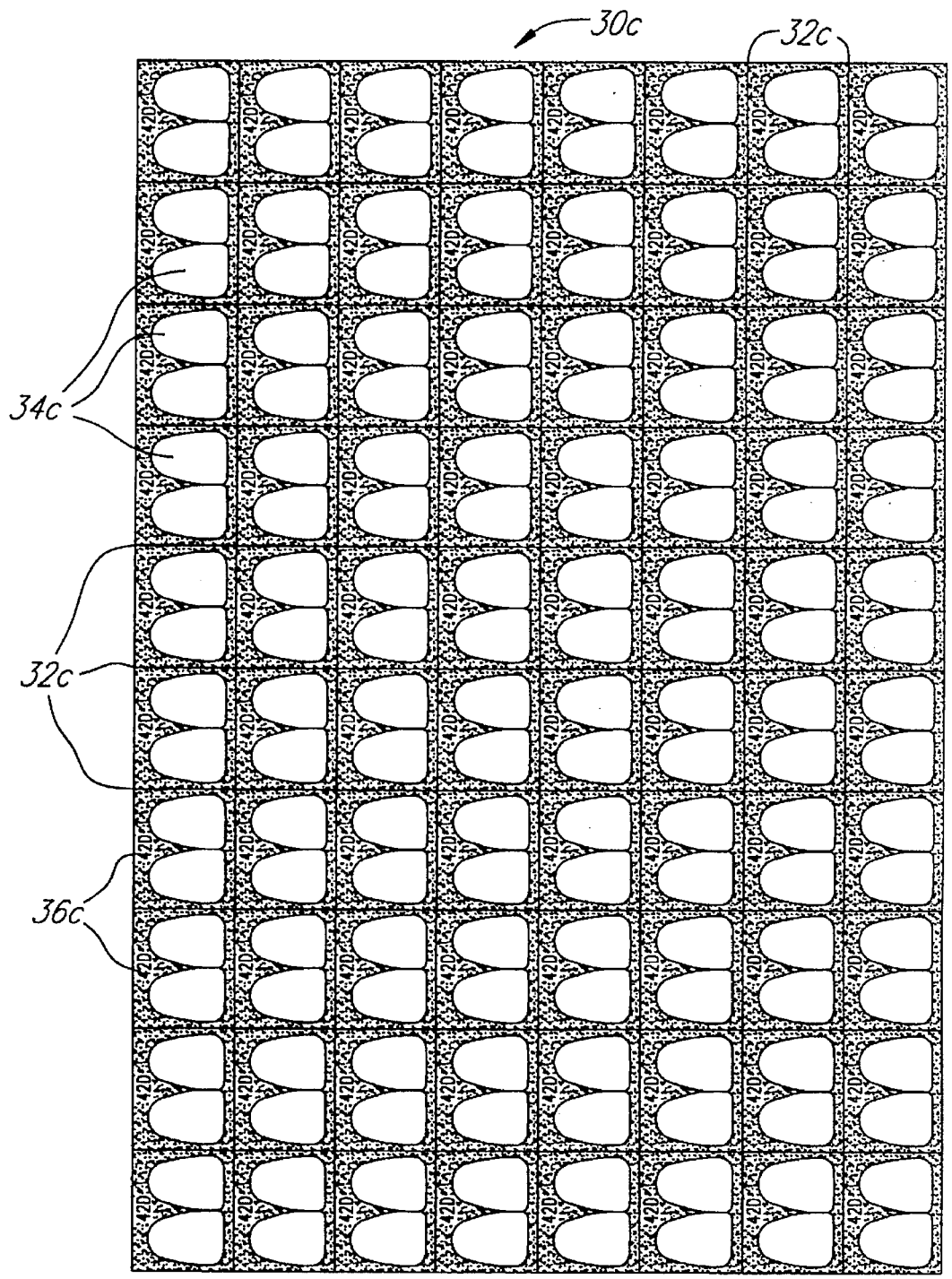
| | WIDTH OF CENTRALS (mm) | LENGTH OF CENTRALS (mm) | WIDTH OF 6 FRONT CENTRALS (mm) |
|---|---|---|---|
| | 8,00 | 10,25 | 46,50 |
TAPERING
42D
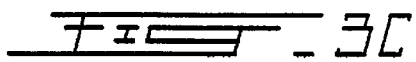

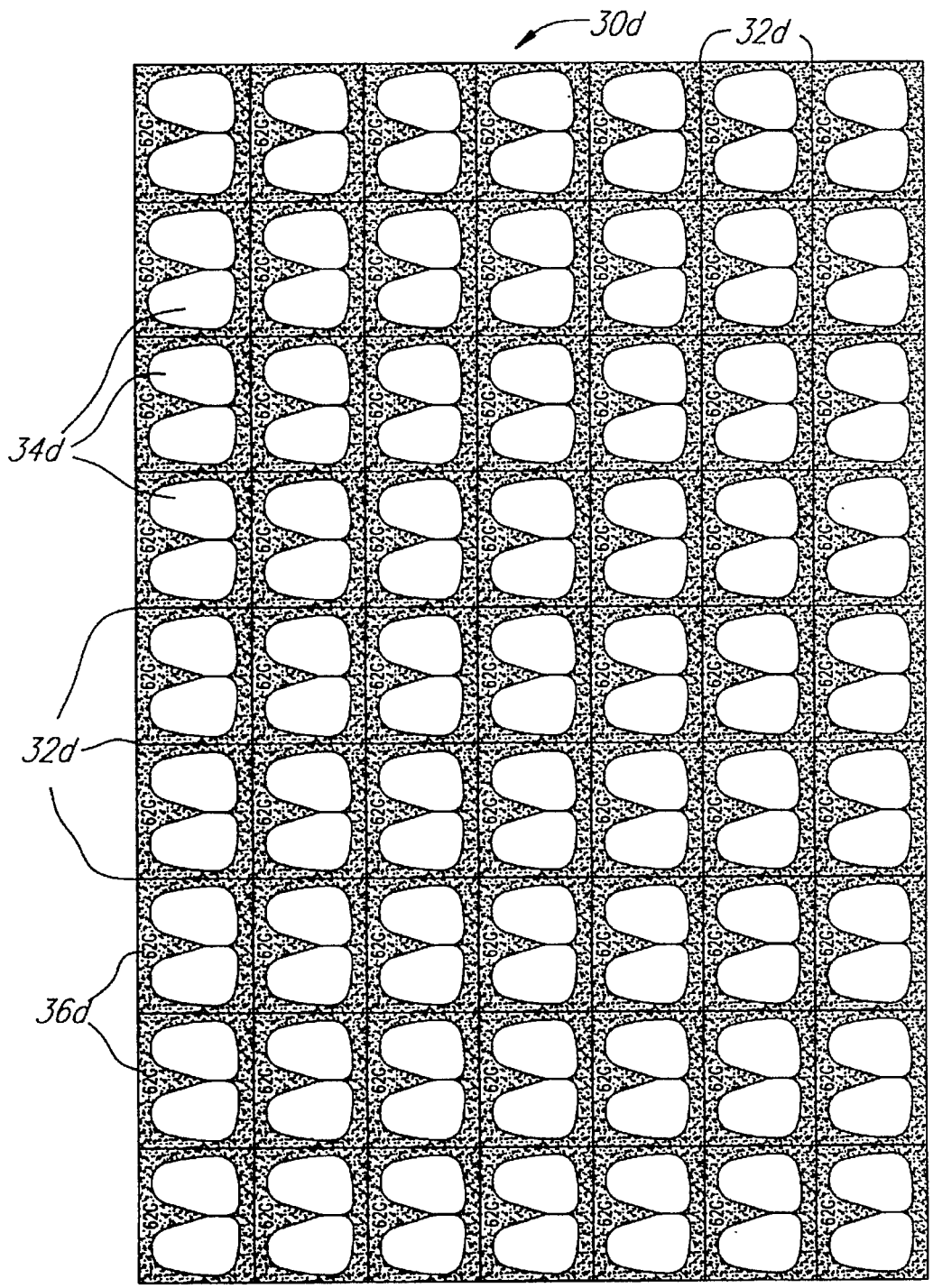

METHOD FOR SELECTING TEETH FOR THE PRODUCTION OF DENTURES OR THE LIKE

BACKGROUND OF THE INVENTION

1. Field of the Invention

The present invention relates to the production of dentures and, more particularly, to a method and a kit for selecting teeth for the production of dentures, or the like. The present invention also relates to a new method for determining the vertical dimension of occlusion with a rest position clearance.

2. Description of the Prior Art

For years, dentures have been made by applying a wax-like or paste-like substance on the gums of the patient to obtain the shape thereof. Depending on the size and configuration of the patient's head and on the shape of the patient's face or mouth, the denturologist will, almost at random while using his experience, select a model of teeth having the shape and size which he considers will be appropriate. On paper, he will set forth the requirements of the teeth and their position on the gum, e.g. angles, etc., and will forward this information to a technician in a laboratory who will produce the dentures or at least the first "draft" thereof.

Then, the dentures are tried in a first fitting on the patient and modifications are necessary in almost every case. The required modifications are then sent back with the dentures by the denturologist to the technician who makes the necessary changes thereto. There is normally three such "fittings" of the dentures on the patient before the dentures become substantially perfectly suited for the patient. This is therefore very costly and time-consuming and the teeth which are only used for the trial dentures (i.e. the first fittings) are then used for dentures of other patients and this can be considered unacceptable hygiene-wise. Furthermore, there is the possibility that a denturologist will consider an early fitting satisfactory, even though the look of the dentures could be improved with respect to the patient's facial characteristics, with a view to decrease the denturologist's cost for the finished dentures.

U.S. Pat. No. 5,004,417 issued to Giaramita on Apr. 2, 1991 discloses a kit and a method comprising sheets of paper 33 on which appear various representations of teeth 35, and also comprising a series of different color pencils used by the dentists and dental laboratory technicians used on the sheets of paper 33 to represent thereon a tooth or a crown which is to be reproduced in a synthetic fashion. The illustration of the tooth or crown is done in order to give the proper color thereto with respect to the color of the surrounding natural teeth. Giaramita mentions that a guide 10 was previously provided in the prior art which comprised a plurality of guide elements 12 removably mounted in a holder 14 and identified with indicia 15. The guide elements 12 are provided with different color shades which can be matched by the dentist with the patient's teeth. Accordingly, the color of the tooth or of the crown is well identified for the dental laboratory technician.

U.S. Pat. No. 3,492,143 issued to Oberg on Jan. 27, 1970 discloses a transfer method for producing artistic colored representations having the appearance of water coloring. The method consists in providing a first sheet of water-resistant material having the outline of a picture thereon; providing an overlay sheet of water-resistant material with the same pictures outlined thereon but in reverse; coloring the picture on the overlay sheet with water soluble coloring material; applying adhesive to areas to be flocked in the picture on the first sheet; applying water absorbent flock material over the adhesive, then wetting the flock material with water preparatary to transfer thereto of the coloring from the coloring material; and, while the second sheet is overlying the first sheet with the pictures in register, pressing the sheets together lightly and only long enough to transfer coloring material from the overlay sheet to the picture on the first sheet without flattening fibers of the flock material.

U.S. Pat. No. 4,738,619 issued to Ross on Apr. 19, 1988 teaches a method and an apparatus for selecting an anchoring device for artificial replacement teeth. The selection of the dental anchor intended to be inserted into a jaw bone of a patient is obtained by using a transparent transfer sheet 10 comprising on one side thereof a series of detachable representations of dental anchors of different sizes. The transfer sheet 10 is superposed on an X-ray 14 in order to position various anchor representations on a location where a dental implant is to be installed. When a pictorial representation of a dental anchor of desired size has been selected, the other side of the transfer sheet 10, opposite the selected pictorial representation, is rubbed so as to transfer this representation on the X-ray 14. Each of the dental anchor representations includes indicia which is indicative of the dimensions of the associated dental anchor.

U.S. Pat. No. 4,294,634 issued to Mookil on Oct. 13, 1991 discloses a method for producing three-dimensional model art statues by using a base shape or body on which are adhesively attached various components. Thereafter, a thin covering of cloth or paper is placed over the body and the components in order to obtain an even finish to the surface thereof.

U.S. Pat. No. 2,169,719 issued to Bush on Aug. 15, 1939 which teaches a method of selecting artificial teeth first describes that, in the prior art, the choice of artificial teeth was made from pictures cut from catalogues which were then positioned on the patient in order to make a selection of an artificial teeth without having to bear the costs associated with maintaining in stock a complete line of artificial teeth. One of the problems of this prior art method resided in the fact that the pictorial representations of the teeth found in these catalogues were not always full size representations. Consequently, Bush discloses a thin transparent flexible strip 1 on which the outlines of various teeth are defined, these teeth corresponding to full size representations of available dental implants. The transparent strip 1 is positioned opposite an edentulous space of the dental arch and it is then possible to determine the shape of the tooth which would be the most appropriate in view of the surrounding teeth and/or of the patient's physiognomy. Indicia are provided on the flexible strip 1 in order to identify the representations of the dental implants appearing thereon.

U.S. Pat. No. 1,458,782 issued to Shapiro on Jun. 12, 1923 teaches a dental apparatus including a plate 10 defining thereon a series of openings 12 and 13; a chart 19 defining dots 19' adapted to correspond to the openings 12 and 13 when the chart 19 is mounted on the plate 10 using pegs 16, 17 and 18; and various artificial crowns 14 each including a dowel 15 adapted to engage the dots 19' and the openings 12 and 13 respectively of the chart 19 and of the plate 10. The artificial crowns 14 can thus be mounted to the plate 10. Seemingly, this apparatus is used by the dentist for presenting the positions of the teeth of a patient in order to then be able to visualize the actual conditions which are encountered and must be overcome. A dentist can thus determine the best appliance to be used after having taken into consideration the conditions of the mouth and can also determine the strains and stresses which will act on the selected appliance.

U.S. Pat. No. 1,338,068 also issued to Bush on Apr. 27, 1920 teaches a method and an apparatus for selecting artificial teeth by using the correlation between the shape of the patient's face and the shape, when inverted, of the two upper central incisors. To that effect, there is provided a plurality of charts 8 preferably formed from a suitable transparent material and having suitably defined thereon a plurality of outlines 9 which correspond to enlarged reproductions of tooth forms in inverted positions. With these charts 8, the dentist can thus choose the appropriate artificial teeth in view of the shape of the patient's face.

U.S. Pat. No. 1,721,526 issued to Moyer on Jul. 23, 1929 discloses a carding system for artificial teeth.

SUMMARY OF THE INVENTION

It is therefore an aim of the present invention to provide a method and an apparatus for selecting artificial teeth for the production of dentures, and the like.

It is also an aim of the present invention to provide a method for the determination of the vertical dimension of occlusion with a rest position clearance.

Therefore, in accordance with the present invention, there is provided a method for determining the size, shape and position of a pair of upper central incisors for the subsequent production of dentures, comprising the steps of:

a) covering at least partly the upper gums of a patient with at least one substance, b) providing a series of representations of pairs of upper central incisors, the representations having different sizes and shapes, c) positioning different ones of the representations on the substance until a representation of desired size and shape has been selected and secured to the substance at a chosen location thereon, and d) removing the substance and the selected representation secured thereto from the patient's mouth.

In a more specific method in accordance with the present invention, the previous method is used for the production of a set of dentures with the following further steps of:

e) using the selected representation for determining the shapes and sizes of the teeth which will form the set of dentures; and f) producing the set of dentures.

Also in accordance with the present invention, there is provided a method for determining the size, shape and position of at least one artificial tooth for the subsequent production of any one of a dental implant, a crown or a bridge, comprising the steps of:

a) covering at least partly the gums and/or partial natural tooth of a patient with at least one substance, b) providing a series of representations of at least one tooth, the representations having different sizes and shapes, c) positioning different ones of the representations on the substance until a representation of desired size and shape has been selected and secured to the substance at a chosen location thereon, and d) removing the substance and the selected representation secured thereto from the patient's mouth.

Further in accordance with the present invention, there is provided a dental kit for determining the size and shape of a pair of upper central incisors for the subsequent production of dentures, comprising a series of representations of pairs of upper central incisors, the representations having different sizes and shapes and being adapted to be positioned in a patient's mouth at a location of the upper central incisors of the dentures, whereby by viewing different ones of the representations, an appropriate pair of upper central incisors can be selected.

In a more specific dental kit in accordance with the present invention, the dental kit further comprises a substantially malleable substance adapted to be applied over the patient's upper gums or over a denture plate secured to the patient's upper gums, adhesive means being provided for securing any selected one of the representations to the substance, whereby once one of the representations has been selected and secured in a desired position on the substance by way of the adhesive means, the substance and the selected representation carried thereby can be removed from the patient's mouth.

Still further in accordance with the present invention, there is provided a dental kit for determining the size and shape of at least one artificial tooth for the subsequent production of any one of a dental implant, a crown or a bridge, comprising a series of representations of at least one tooth, the representations having different sizes and shapes and being adapted to be positioned in a patient's mouth at a location for the dental implant, crown or bridge, whereby by viewing different ones of the representations, an appropriate artificial tooth can be selected.

In a more specific construction in accordance with the present invention, the previous dental kit further comprises a substantially malleable substance adapted to be applied over the patient's gums and/or partial natural tooth, adhesive means being provided for securing any selected one of the representations to the substance, whereby once one of the representations has been selected and secured in a desired position on the substance by way of the adhesive means, the substance and the selected representation carried thereby can be removed from the patient's mouth.

Still further in accordance with the present invention, there is provided a method for determining the vertical dimension of occlusion with a rest position clearance for the subsequent production of dentures, comprising the steps of:

a) covering at least partly the lower gums of a patient with at least one substance, b) having the patient produce a maximum natural smile and tracing on said substance a line corresponding to an upper outline of the patient's lower lip during the maximum natural smile, the line corresponding to the upper edges of the lower incisors of the dentures minus approximately 2 mm, whereby the lower incisors will extend approximately 2 mm above the patient's lower lip during the maximum natural smile.

Also in accordance with the present invention, in the previous method, the lower incisors are centered by using a vertical line traced between a pair of upper central incisors selected as follows:

covering at least partly the upper gums of the patient with at least one further substance, providing a series of representations of pairs of upper central incisors, the representations having different sizes and shapes, positioning different ones of the representations on the further substance until a representation of desired size and shape has been selected and secured to the further substance at a chosen location thereon.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is a schematic chart showing four typical classes of human teeth shapes;

FIGS. 2A, 2B, 2C and 2D represent charts showing various pairs of upper central incisors and the identification and dimensions thereof respectively for the following four general shapes of teeth: square, square-tapering, tapering, and ovoid;

FIGS. 3A, 3B, 3C and 3D represent templates in accordance with the present invention each including a series of frangible cutouts each illustrating a pair of upper central incisors of a same particular size, the four Figures each pertaining to a respective one of the model teeth shown in FIGS. 2A to 2D;

DESCRIPTION OF THE PREFERRED EMBODIMENTS

With reference to FIG. 1, there are generally four typical classes of human face shapes or outlines, commonly termed the square, square-tapering, tapering and ovoid forms. In FIG. 1, these four different forms are represented on four different rows. In upper first row 10, two generally square-shaped human faces are illustrated at 10a and 10b with, at 10c, a grid being superposed over the human face to show the square configuration thereof, and with a schematic representation of 10c being shown at 10d.

Similarly, there are shown various square-tapering contours of human faces and, more particularly, two typical square-tapering faces are shown at 12a and 12b with, at 12c, a grid being superposed over the human face to show the contour thereof, followed by a schematic representation of this contour at 12d.

In third row 14, two human faces 14a and 14b are shown for illustrating human faces having a tapering contour, with a grid being superposed on a tapering human face at 14c for better illustrating the taper, followed by a schematic representation of the tapering contour at 14d.

In bottom row 16, two human faces having a substantially ovoid contour are shown at 16a and 16b with, at 16c, a grid being superposed on a human face to better illustrate the ovoid outline thereof, and with a schematic representation of the ovoid contour on a human face being shown at 16d.

It is noted that further categories exist for classifying the various shapes of the human face, such as the square-ovoid and the square-ovoid-tapering outlines.

FIG. 2A illustrates a chart 20a which shows, on seven different lines, seven models of upper central incisors of the square-type, which are thus associated with human faces such as those shown in row 10 of FIG. 1. In chart 20a, the first column includes the identification or model number of a specific pair of "square" upper central incisors, with the second and third columns showing respectively the width and the length (in millimeters) of each of the incisors of the pair of upper central incisors of the respective row. The fourth column indicates the arcuate width, in millimeters, of the sixth upper front teeth, with the fifth column showing the pair of upper central incisors associated with a respective identification number of the first column.

Figure 2B:

Similarly, FIGS. 2B, 2C and 2D include respectively charts 20b, 20c and 20d which are substantially identical to chart 20a of FIG. 2A, although charts 20b, 20c and 20d respectively pertain to upper central incisors respectively of the square-tapering, tapering and ovoid types.

FIG. 3A, in accordance with the present invention, illustrates a template 30a which includes a series of frangible cutouts each showing a same pair of upper central incisors which, in the illustration, corresponds to the central incisors "11D" of the first row of the chart 20a of FIG. 2A. Similar templates are provided (although not shown) for the remaining sizes of "square" teeth which are available such as the remaining models of FIG. 2A and also other "square" models not illustrated in FIG. 2A. Similarly, FIG. 3B illustrates a template 30b which includes a plurality of detachable representations of a same pair of upper central incisors of the square-tapering type. The template 30b corresponds to the teeth model "21C" of the first line of chart 20b of FIG. 2B. Again, similar templates are provided for other square-tapering sizes of upper central incisors.

FIGS. 3C and 3D respectively illustrate templates 30c and 30d which each include a plurality of detachable representations of a same pair of upper central incisors. In FIG. 3C, the tapering upper central incisors which are illustrated correspond to model "42D" of the first line of the chart 20c of FIG. 2C. The teeth model illustrated in FIG. 3D is of the ovoid type illustrated in the only line of chart 20d of FIG. 2D.

In FIGS. 3A to 3D, the frangible lines are identified by reference numeral 32 with the appropriate one of the suffixes "a", "b", "c" or "d". Each separate representation of a pair of upper central incisors on each of the templates 30a to 30d are identified by the reference numeral 34 with the appropriate suffix "a", "b", "c" or "d". Finally, on each of the representations 34a to 34d of FIGS. 3A to 3D, the model number of the illustrated pair of upper central incisors is respectively indicated at 36a, 36b, 36c and 36d for identification purposes of the representations 34a, 34b, 34c and 34d especially when these representations are detached from their respective templates 30a to 30d. As seen in FIGS. 3A to 3D, the templates 30a to 30d include respective borders 38a, 38b, 38c and 38d each identifying the shape of the teeth which are illustrated thereon, the identification number thereof and the various dimensions thereof.

The templates 30a to 30d and thus the respective individual representations 34a to 34d thereof represent a mainly two-dimensional representation of the upper central incisors which are available for the production of dentures, or the like. The individual representations 34a to 34d of templates 30a to 30d are, in the illustrated embodiment, plastic-laminated black and white photographs of artificial model teeth.

To accompany the templates 30a to 30d, there is also provided in accordance with the present invention, a wax-like roll which, before use, takes the shape of a rectangular sheet of wax-like material which is heated and then applied on the gums of the patient. Thereafter, the roll is manipulated so as to take the form of the gums. With reference to FIGS.

Figure 5:
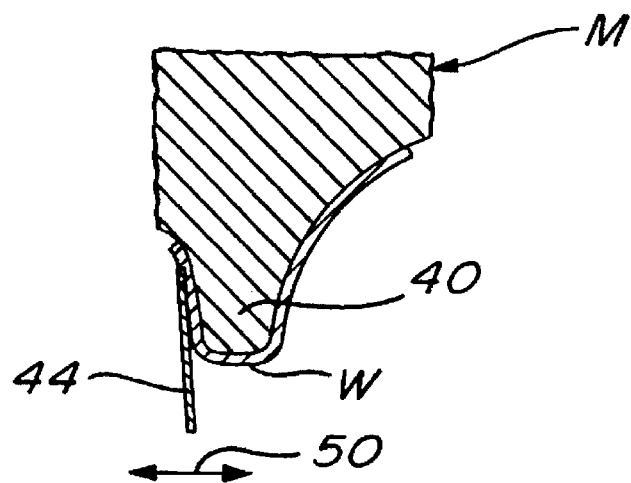
FIG. 5 is a cross-sectional side view taken along lines 5—5 of FIG. 4.

4 and 5, a mouth M of a patient includes upper and lower gums 40 and 42, respectively. Wax W has been applied in order to cover the upper gums 40 and follow the contour thereof, as best seen in FIG. 5.

Figure 4:
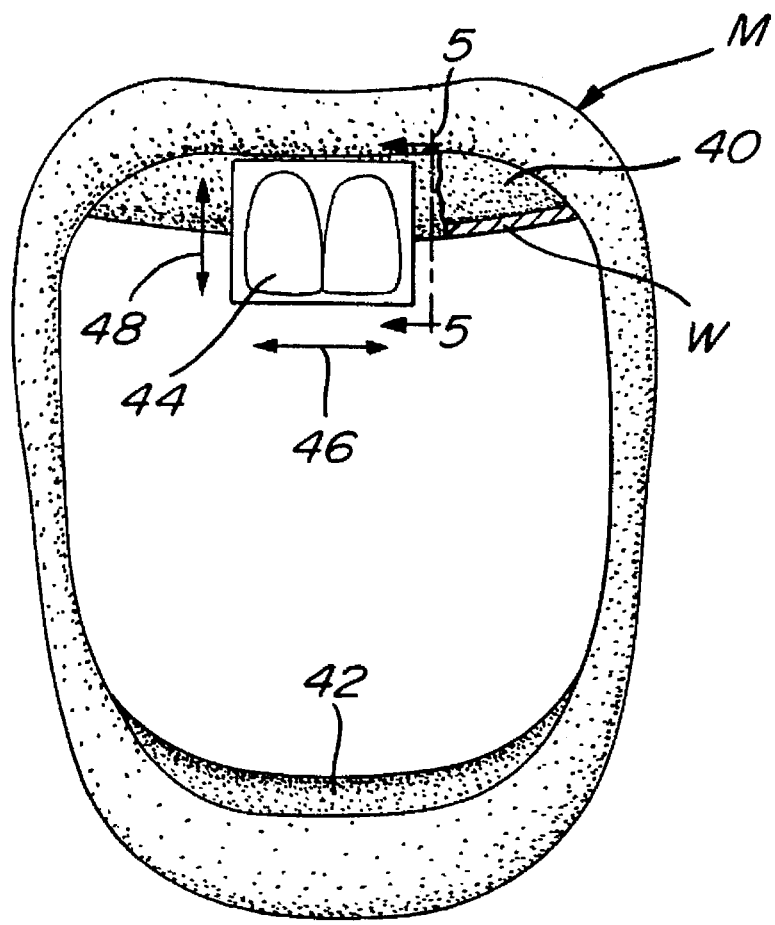
FIG. 4 is a schematic fragmented elevation of a mouth onto which a two-dimensional representation of a pair of upper incisors taken from one of the templates of FIGS. 3A to 3D is applied on the upper gums of the patient with an adhesive for visualizing and selecting proper artificial teeth therefor in accordance with a method and an apparatus in accordance with the present invention.

Once the wax W has been applied on the upper gums 40 of the patient and after a general shape of the upper central incisors for this particular patient has been chosen (for example, by way of various known methods, such as that disclosed in aforementioned U.S. Pat. No. 1,338,068), the dentist or denturologist will select an appropriate template, such as templates 30a to 30d or any further templates illustrating other sizes or shapes of upper central incisors, and will detach therefrom a representation, such as one of the representations 34a to 34d of FIGS. 3A to 3D. The selected representation, which is identified by the reference numeral 44 in FIGS. 4 and 5, is applied on the wax with enough pressure so that the selected representation 44 adheres thereto, as illustrated in FIGS. 4 and 5. It is then possible for the dentist or denturologist to visualize his choice of the upper central incisors directly on the patient. With various trials of different representations taken from different templates, the dentist or denturologist will come to choose the most appropriate model of upper central incisors for a particular patient. The dentist or denturologist can also appropriately position the selected representation 44 substantially perfectly on the roll of wax W by moving the representation 44 with respect to the upper gums 40 vertically along arrows 46, horizontally along arrows 48 and/or forward or rearward along arrows 50.

Once the dentist or denturologist has finalized his choice of the shape and size of the upper central incisors for a particular patient and once the representation of this teeth model has been appropriately positioned on the roll of wax W, the dentist or denturologist can send to the dental laboratory technician a standard plaster mold of the patient's gums as well as the roll of wax W and the selected representation 44 appropriately attached thereto. As the roll of wax W can then be positioned over the plaster mold of the upper gums of the patient in a closely fitting fashion, the technician is able to see the selected representation 44 exactly as the dentist or denturologist saw this representation 44 on the patient. This will allow the laboratory technician to produce a denture not only based on the appropriate size and shape of the upper central incisors but also on the appropriate positioning thereof with respect to the gums. It is noted that the models of the remaining teeth which will be part of the dentures all result from the choice of the upper central incisors.

With the present method and apparatus, it becomes easy for the dentist or denturologist to economically try a series of different models of teeth without having in stock a plurality of three-dimensional teeth models. By adhesively mounting the selected representation 44 to, in the illustrated embodiment, a roll of wax W covering the upper gums 40 of the patient, the present invention eliminates any interpretation by the laboratory technician of the positioning of the upper central incisors with respect to the upper gums of the patient. The dentist or denturologist, in addition to selecting with more ease an appropriate model of upper central incisors, can accurately position the selected teeth representation 44 for the technician's benefit. On one hand, the use of two-dimensional representations allow for the dentist or denturologist to try various models of teeth directly in the mouth of the user until the most appropriate set of teeth is chosen; on the other hand, by adhesively mounting the selected representation 44 to a roll of wax W at a best possible location in view of the patient's mouth and face, there remains substantially no error in the positioning of the selected teeth on the dentures by the technician. Indeed, the technician, as opposed to prior art techniques, sees the same draft dentures as the denturologist thereby substantially eliminating the technician's interpretations of the denturologist instructions, notes, schematic representations, etc. With the present method, the first dentures produced by the technician produce normally a perfect fit on the patient and there are no surprises as to the look of the dentures in the mouth of the patient when they are tried for the first time. The present method thus eliminates the numerous fittings and consequently it reduces the cost of the dentures and the time required to produce the same. Therefore, this results in better looking dentures which, normally, will not require two, three or even four fittings. Furthermore, there is no more need to maintain in stock a larger number of model teeth, which are expensive. Moreover, no artificial teeth rejected from a first denture are used for producing the dentures of another patient.

As the representations 34a to 34d or the selected representation 44 include thereon an identification of the model of teeth, such as the identifications 36a to 36d of the representations 34a to 34d of FIGS. 3A to 3D, the technician has, with the combination of the selected representation 44 and the roll of wax W, the remaining information concerning the selected model of upper central incisors. The dentist or denturologist can even write notes on the white portions of the selected representation 44, such as the colour of the teeth which should be used for the production of the dentures.

The present method can also be used for the production of crowns and bridges. In such cases, 2-D model teeth can be positioned on the plaster mold of the patient's gums and teeth, thereby allowing a direct evaluation of the choice by comparison with the adjacent teeth defined on the mold.

It is also noted that prior to the application of the wax W, a denture plate can be fitted on the upper gums 40 of the mouth M of the patient. A denture plate represents the part of an artificial set of teeth that fits to the gums of the mouth and holds the teeth in place. Since the denture plate can firmly be secured to the upper gums 40 of the patient as such a denture plate is configured exactly as these upper gums 40, it becomes often easier to apply the wax W as it is applied on the denture plate and not directly on the upper gums 40 of the patient.

It is further noted that an adhesive can be used for attaching the representations 34 of the upper central incisors to the wax W.

Also, when the chosen representation 34a, 34b, 34c or 34d (or any other appropriate representation) is secured to the wax W which itself is mounted over the denture plate, the laboratory technician will already have in hand the denture plate and the relative positioning of the chosen representation with respect thereto for easy production of dentures identical to what the denturologist or dentist saw in the patient's mouth during the process of selection and positioning of the representation on the patient's upper gums 40.

Figure 6:
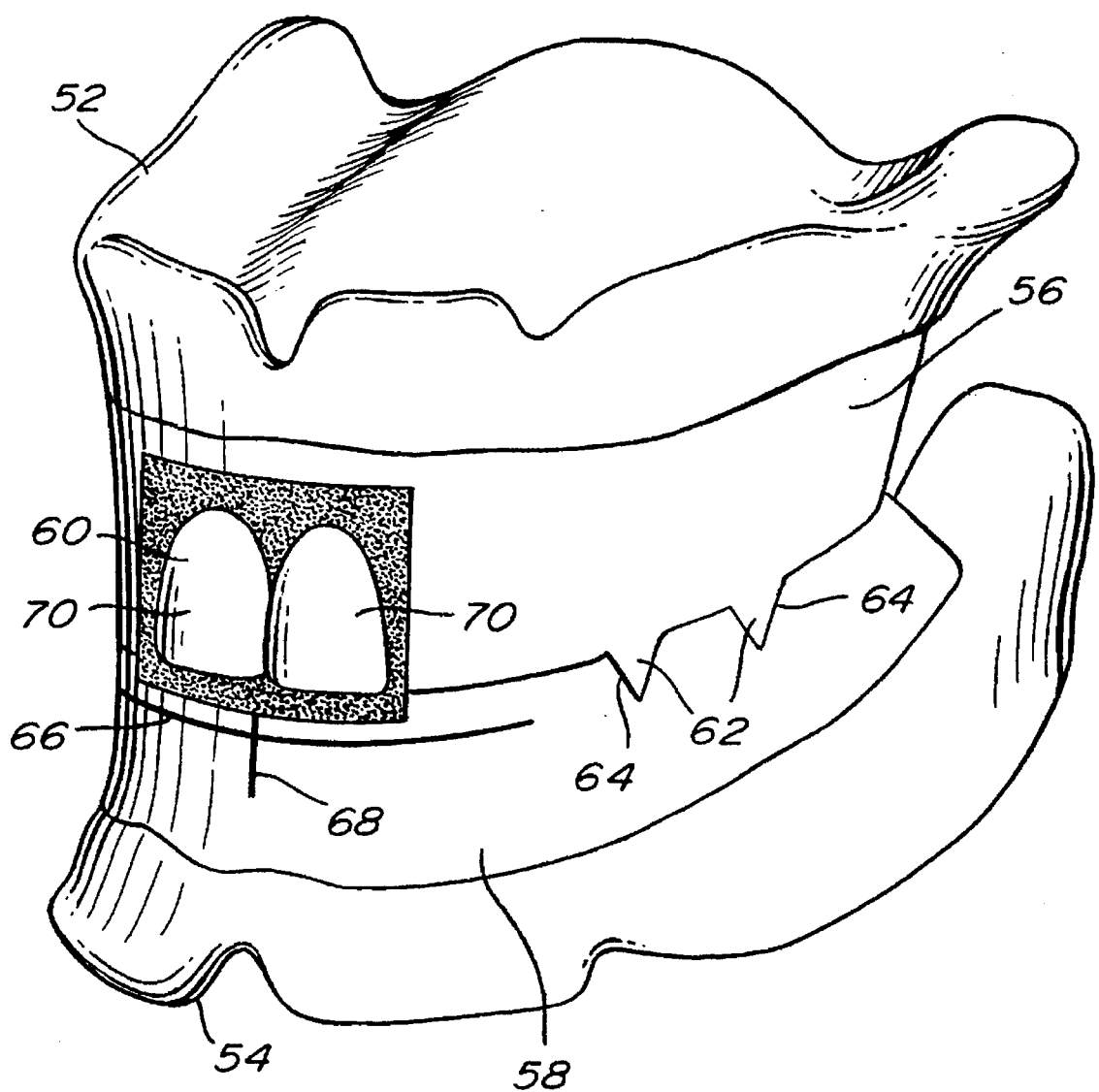
FIGS. 6 and 7 represent respectively a schematical perspective view and a schematical side elevational view which both pertain to a method in accordance with the present invention for determining the vertical dimension of occlusion with a rest position clearance.
Figure 7:
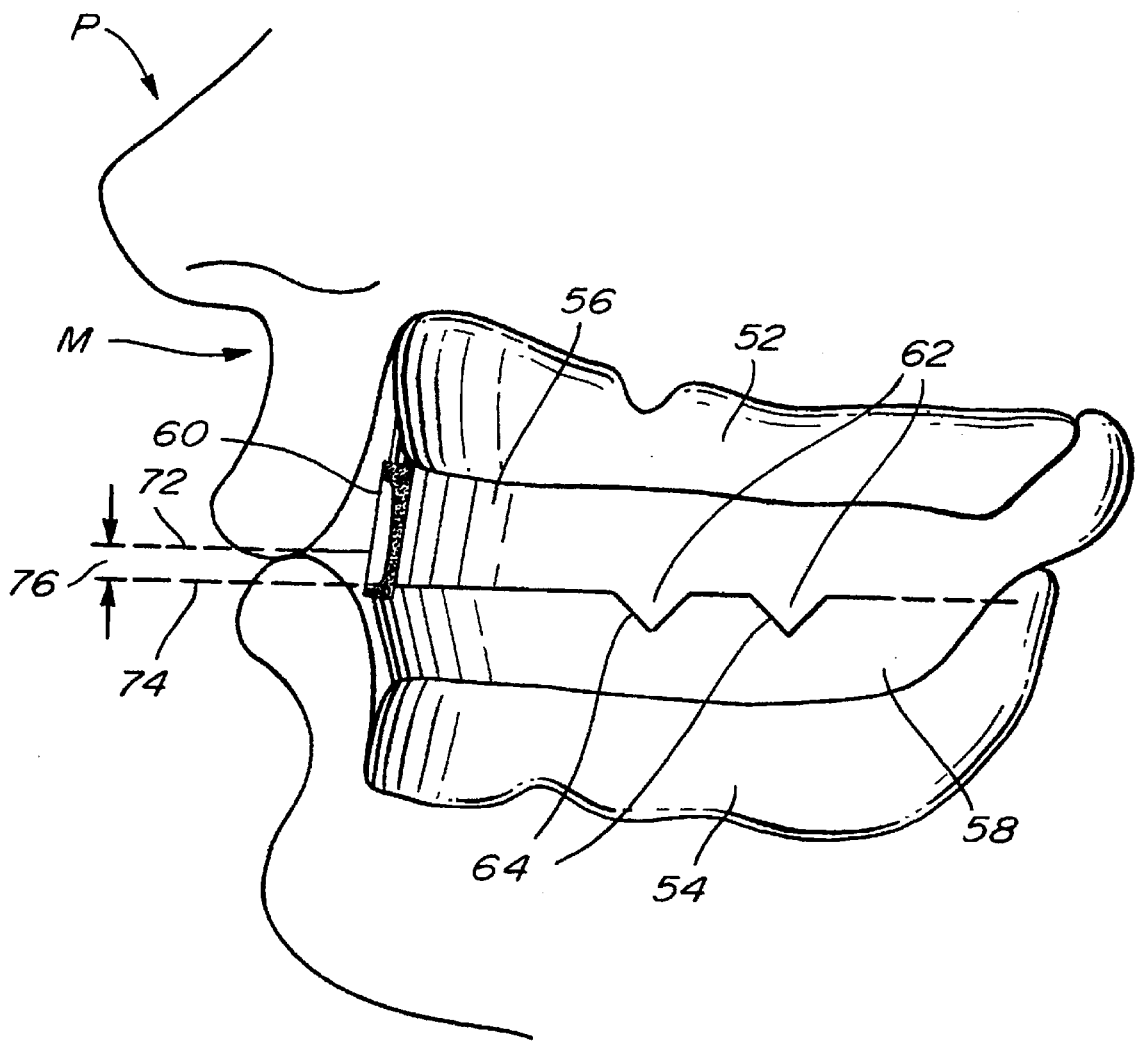

Also in accordance with the present invention, FIGS. 6 and 7 are illustrations which pertain to a method for determining the vertical dimension of occlusion with a rest position clearance. More particularly, when a patient's mouth M is closed in a rest position thereof, a rest position clearance between the upper and lower central incisors varies approximately between 2 and 3 mm. In other terms, in this rest position, the upper horizontal edge of the lower central incisors extends 2 to 3 mm above the lower horizontal edge of the upper central incisors.

Once the model of the upper central incisors has been determined by the apparatus and method of FIGS. 1 to 5, the remaining teeth of both the upper and lower dentures are also determined, as mentioned hereinbefore. However, it is still necessary to determine the position of the lower central incisors with respect to the upper central incisors. This is achieved with the present method for determining the vertical dimension of occlusion with a rest position clearance.

More particularly, with reference to FIG. 6, upper and lower denture plates 52 and 54 are prepared to fit over the patient's upper and lower gums 40 and 42, respectively. Two rolls of wax W, that is an upper roll 56 and a lower roll 58, are applied respectively on the upper and lower denture plates 52 and 54. On the upper roll of wax 56, a representation 60 of a pair of upper central incisors has been chosen and positioned using the method and apparatus of FIGS. 1 to 5. Then, the lower roll of wax 58 is positioned on the lower denture plate 54. Afterwards, the patient is asked to bite lightly on the rolls of wax 56 and 58. In order to ensure the proper relative position of the upper and lower rolls of wax 56 and 58 at all times during the procedure, the upper and lower rolls of wax 56 and 58 define mating tongue and groove arrangements which are illustrated in FIG. 6 by a pair of downwardly extending V-shaped protrusions 62 defined on the upper roll 56 and which engage a pair of corresponding V-shaped notches 64 defined in the lower roll of wax 58.

Then, the patient is asked to produce a maximum natural smile and a line 66 is traced on the lower roll of wax 58 which corresponds to the upper contour of the patient's lower lip. This line 66 corresponds to the height of the lower central incisors minus two millimeters. In other words, the upper horizontal edges of the lower central incisors will extend approximately two millimeters above the line 66. Also, the lower central incisors will thus extend two millimeters above the patient's lower lip when the patient's mouth is in the position thereof of maximum natural smile. Accordingly, the lower central incisors are easily positionable on the lower roll of wax 58.

Furthermore, a vertical line 68 is traced between the two upper central incisors 70 of the two-dimensional representation 60. The vertical line 66 is used for properly centering the lower central incisors on the lower roll of wax 58. Therefore, line 66 permits the vertical positioning of the lower central incisors, whereas line 68 ensures a proper horizontal centering thereof.

Now referring to FIG. 7, a patient P has his/her mouth M thereof in a rest position. Line 72 corresponds to the upper edges of the lower central incisors, whereas line 74 corresponds to the lower edges of the upper central incisors. A distance 76 defined between lines 72 and 74 represents the rest position clearance which varies between 2 and 3 millimeters.

Accordingly, with the apparatus and methods of the present invention, the production of dentures is greatly simplified while increasing the aesthetic results thereof.

The embodiments of the invention in which an exclusive property or privilege is claimed are defined as follows:

1. A method for determining the size, shape and position of a pair of upper central incisors for the subsequent production of dentures, comprising the steps of:
    a) covering at least partly the upper gums of a patient with at least one substance,
    b) providing a series of representations of pairs of upper central incisors, said representations having different sizes and shapes,
    c) positioning different ones of said representations on said substance until a representation of desired size and shape has been selected and secured to said substance at a chosen location thereon, and
    d) removing said substance and said selected representation secured thereto from the patient's mouth.

2. A method as defined in claim 1, wherein said representations each include thereon indicia indicative of the size of the upper central incisors represented thereon.

3. A method as defined in claim 2, wherein said indicia are also indicative of the general shape of the upper central incisors associated therewith.

4. A method as defined in claim 1, wherein said series of representations are provided on at least one template means, each representation being detachable from said template means.

5. A method as defined in claim 4, wherein a different template means is provided for each different representations, whereby each template means comprises a plurality of substantially identical representations which are detachable one by one therefrom.

6. A method as defined in claim 1, wherein said representations appear on a substantially two-dimensional medium which is adapted to be secured to said substance in step c).

7. A method as defined in claim 1, wherein said substance is a wax-like material applied on the patient's upper gums.

8. A method as defined in claim 1, wherein said substance comprises a denture plate adapted to be applied on the patient's upper gums and a wax-like material adapted to be applied on said denture plate, said representations being secured in step c) to said wax-like material.

9. A method for determining the size, shape and position of a pair of upper central incisors and for producing a set of dentures based thereon as defined in claim 1 and further comprising the steps of:
    e) using said selected representation for determining the shapes and sizes of the teeth which will form said set of dentures; and
    f) producing said set of dentures.

10. A method for determining the size, shape and position of at least one artificial tooth for the subsequent production of any one of a dental implant, a crown or a bridge, comprising the steps of:
    a) covering at least partly the gums and/or partial natural tooth of a patient with at least one substance,
    b) providing a series of representations of at least one tooth, said representations having different sizes and shapes,
    c) positioning different ones of said representations on said substance until a representation of desired size and shape has been selected and secured to said substance at a chosen location thereon, and
    d) removing said substance and said selected representation secured thereto from the patient's mouth.

11. A dental kit for determining the size and shape of a pair of upper central incisors for the subsequent production of dentures, comprising a series of representations of pairs of upper central incisors and representation securing means, said representations having different sizes and shapes and being adapted to be positioned in a patient's mouth at a location of the upper central incisors of the dentures and to be temporarily installed in the patient's mouth with said securing means, whereby by viewing different ones of said representations, an appropriate pair of upper central incisors can be selected.

12. A dental kit as defined in claim 11, wherein said securing means comprise a substantially malleable substance adapted to be applied over the patient's upper gums or over a denture plate secured to the patient's upper gums and adhesive means for securing any selected one of said representations to said substance, whereby once one of said representations has been selected and secured in a desired position on said substance by way of said adhesive means, said substance and said selected representation carried thereby can be removed from the patient's mouth.

13. A dental kit as defined in claim 11, wherein said representations each include thereon indicia indicative of the size of the upper central incisors represented thereon.

14. A dental kit as defined in claim 13, wherein said indicia are also indicative of the general shape of the upper central incisors associated therewith.

15. A dental kit as defined in claim 11, wherein said series of representations are provided on at least one template means, each representation being detachable from said template means.

16. A dental kit as defined in claim 15, wherein a different template means is provided for each different representations, whereby each template means comprises a plurality of substantially identical representations which are detachable one by one therefrom.

17. A dental kit as defined in claim 12, wherein said representations appear on a substantially two-dimensional medium which is adapted to be secured to said substance.

18. A dental kit as defined in claim 12, wherein said substance and said adhesive means are wax-like materials.

19. A dental kit for determining the size and shape of at least one artificial tooth for the subsequent production of any one of a dental implant, a crown or a bridge, comprising a series of representations of at least one tooth and representation securing means, said representations having different sizes and shapes and being adapted to be positioned in a patient's mouth at a location for the dental implant, crown or bridge and to be temporarily installed in the patient's mouth with said securing means, whereby by viewing different ones of said representations, an appropriate artificial tooth can be selected.

20. A dental kit as defined in claim 19, wherein said securing means comprise a substantially malleable substance adapted to be applied over the patient's gums and/or partial natural tooth and adhesive means for securing any selected one of said representations to said substance, whereby once one of said representations has been selected and secured in a desired position on said substance by way of said adhesive means, said substance and said selected representation carried thereby can be removed from the patient's mouth.

21. A dental kit as defined in claim 20, wherein a portion of a denture plate is provided for application, in cases of bridges and dental implants, on the patient's gums at the location of the intended bridge or dental implant, said malleable substance being adapted to be applied over said dental plate portion before said different ones of said representations are viewed in the patient's mouth and finally secured to said malleable substance by way of said adhesive means.

22. A method for determining the vertical dimension of occlusion with a rest position clearance for the subsequent production of dentures, comprising the steps of:
  a) covering at least partly the lower gums of a patient with at least one substance,
  b) having the patient produce a maximum natural smile and tracing on said substance a line corresponding to an upper outline of the patient's lower lip during said maximum natural smile, said line corresponding to the upper edges of the lower incisors of the dentures minus approximately 2 mm, whereby the lower incisors will extend approximately 2 mm above the patient's lower lip during said maximum natural smile.

23. A method as defined in claim 22, wherein the lower incisors are centered by using a vertical line traced between a pair of upper central incisors selected as follows:
  covering at least partly the upper gums of the patient with at least one further substance,
  providing a series of representations of pairs of upper central incisors, said representations having different sizes and shapes,
  positioning different ones of said representations on said further substance until a representation of desired size and shape has been selected and secured to said further substance at a chosen location thereon.

* * * * *